United States Patent [19]

Prasad

[11] Patent Number: 5,091,148
[45] Date of Patent: Feb. 25, 1992

[54] TITANIUM ALLOY DENTAL RESTORATIONS

[75] Inventor: Arun Prasad, Chesire, Conn.

[73] Assignee: Jeneric/Pentron, Inc., Wallingford, Conn.

[21] Appl. No.: 636,912

[22] Filed: Jan. 2, 1991

[51] Int. Cl.$^5$ .............................................. C22C 14/00
[52] U.S. Cl. .................................. 420/417; 420/421; 606/78
[58] Field of Search .................... 420/417, 421; 606/78

[56] References Cited

U.S. PATENT DOCUMENTS

| | | | |
|---|---|---|---|
| 4,040,129 | 8/1977 | Steinemann et al. | 420/417 |
| 4,170,990 | 10/1979 | Baumgart et al. | 606/78 |
| 4,197,643 | 4/1980 | Burstone et al. | 420/421 |
| 4,253,933 | 3/1981 | Sato et al. | 420/417 |
| 4,666,666 | 5/1987 | Taki et al. | 420/417 |
| 4,810,465 | 3/1989 | Kimura et al. | 420/417 |
| 4,857,269 | 8/1989 | Wang et al. | 420/417 |
| 4,859,415 | 8/1989 | Shida et al. | 420/417 |

OTHER PUBLICATIONS

Van Noort, Jour. Mat. Sci., 22 (1987), 3801.

*Primary Examiner*—Upendra Roy
*Attorney, Agent, or Firm*—Perman & Green

[57] ABSTRACT

Improved titanium alloys for dental castings and processes for the preparation thereof, characterized by the incorporation of predetermined small amounts of one or more noble metals, preferably ruthenium, or rhenium, and optional predetermined small amounts of one or more rare earth metals, preferably cerium. The present alloys have improved corrosion and tarnish resistance under the conditions of use, and the preferred compositions including rare earth metals have improved oxidation resistance which improves their receptivity and bonding strength for enamels, porcelain surfacing materials or caps.

11 Claims, No Drawings

TITANIUM ALLOY DENTAL RESTORATIONS

BACKGROUND OF THE INVENTION

1. Field of Invention

The present invention relates to improvements in the use of titanium alloys for the casting of dental restorations such as inlays, crowns, bridges and other dental prosthetic appliances having resistance of corrosion and oxidation under the conditions to use. According to one embodiment, the present invention relates to improved titanium alloys for the casting of dental restoration having improved receptivity and bonding strength for porcelain surfacing materials such as enamels or caps applied thereto to simulate the surface appearance of teeth.

2. Description of the Prior Art

It is well known to cast dental restorations from pure titanium and certain titanium alloys in place of noble metals such as gold and silver and alloys thereof, which are expensive and have other disadvantages such as softness, which make them susceptible to surface abrasion and distortion during use.

U.S. Pat. Nos. 4,700,769; 4,709,741; 4,768,757; 4,830,083 and 4,830,823 disclose the advantages and disadvantages of pure titanium and certain titanium alloys used for casting dental restorations.

As disclosed in U.S. Pat. No. 4,768,757, pure titanium and certain titanium alloys provide dental castings having surfaces which are soft and abrasive. A post-treatment with a nitrogen gas is required to nitride the titanium surface to increase the surface hardness and its resistance to surface abrasion.

As disclosed in U.S. Pat. Nos. 4,700,769; 4,709,741 and 4,830,083, titanium and the known titanium dental alloys are very susceptible to oxidation and require certain mold materials to prevent contamination of the dental casting and severe degradation of its physical properties, which render its unfit for its intended use.

As disclosed in U.S. Pat. No. 4,830,823 certain titanium alloys for dental castings, such as Ti-6Al-4V, are hard and brittle and require a troublesome heat aftertreatment under vacuum which has precluded their practical use for dental castings. Said Patent discloses new alloys of titanium, aluminum and vanadium, specific ones of which have improved physical characteristics such as tensile strength and hardness. However the new alloys contain the same metal ingredients of Ti-6Al-4V and suffer from the same lack of resistance to oxidation.

Titanium generally is considered resistant to corrosion attack in oxidizing, neutral and inhibited reducing conditions, due to the formation of a protective surface oxide film. However, in the case of dental castings, such surface oxide films are undesirable because they tarnish the surface of the castings and interfere with the bonding properties of the surface of the castings for after-applied ceramic or porcelain surface coatings, enamels or caps applied thereover to cover or mask the metallic surface.

Titanium corrodes very rapidly in acid fluoride environments and therefore is susceptible to attack by fluoride chemicals present in toothpaste, mouthwash or liquid fluoride coatings applied to harden teeth and reduce dental carries. While mouth acidity and fluoride concentration are low, surface corrosion and surface tarnish are problems in the case of dental castings of pure titanium and the titanium alloys known for dental casting use.

SUMMARY OF THE INVENTION

The present invention relates to the discovery of novel titanium alloys which are well suited for the casting of dental restorations having excellent properties of abrasion-resistance, and resistance to corrosion and oxidation, and which have excellent receptivity and bonding strength for porcelain or other ceramic surfacing materials.

The invention also includes the improved dental restorative materials and the methods for casting them.

The novel dental alloy compositions of the present invention comprise a base of pure titanium, or of any of the titanium alloys known for use as dental alloys, or of alloys of titanium, aluminum and a third metal from the group consisting of tin, niobium and vanadium, to which is added a small amount of one or more noble metals and/or rhenium, and/or one or more rare earth elements.

The preferred specific titanium alloys for modification according to the present invention include titanium-aluminum-tin alloys, such as Ti-5Al-2Sn. Tin is a solid-state strengthener and retards diffusion. Also included are titanium-aluminum-niobium alloys, such as Ti-6Al-7Nb; titanium-aluminum-vanadium alloys, such as Ti-6Al-4V and Ti-1.5 to 4 Al-1 to 3V, and other biocompatible titanium alloys known for dental alloy use.

The alloying one or more noble metals, and/or rhenium, with titanium or its alloys produces a new alloy having improved corrosion-resistance under the conditions of use. These alloys produce uniform, dense dental restorations and appliances having smooth, non-abrasive cast surfaces which are more resistant to corrosion because of their chemical composition. Noble metals are inert and generally resistant to corrosion. They also increase the ductility of the titanium alloy. A preferred noble metal is ruthenium, because it is relatively inexpensive and oxidation-resistant. Rhenium is an additive which is alternative or cumulative to the noble metal to improve the corrosion resistance of the titanium alloy, possibly by improving its fine grain structure to provide dental castings having smoother surfaces free of microvoids and less susceptible to corrosive attack.

The addition of one or more rare earth elements, such as cerium, increases the resistance of the alloy to surface oxidation. This is particularly important in cases where the titanium alloy restorations or appliances are to be bonded to dental enamels, porcelains or caps. Avoidance of the formation of surface oxides of titanium is desirable because such oxides are weakly-bonded to the alloy and provide a weak bond for enamels, porcelain coatings or caps which are after-applied over the metal restoration in order to mask its presence.

DESCRIPTION OF THE PREFERRED EMBODIMENT

The novel dental casting alloys of the present invention comprise alloys of pure titanium, or of titanium dental alloys with:

(a) 0.01 to 5.0%, most preferably 0.1 to 1.0% by weight of a noble metal and/or of rhenium and (b) 0 to 5%, most preferably 0.01 to 1.0% by weight of a rare earth metal.

As discussed supra, the additive (a) imparts improved corrosion resistance when alloyed with pure titanium or with the aforementioned alloys of titanium.

Suitable additives (a) are the noble metals such as gold, silver, platinum, palladium and ruthenium, and rhenium. The preferred additives (a) are the noble metal ruthenium, and rhenium, and mixtures thereof.

As also discussed above, the optional additive (b) imparts unproved oxidation resistance when alloyed with pure titanium or with the aforementioned alloys of titanium.

The preferred rare earth metal additive is cerium, but yttrium and hafnium are also suitable.

Alloy composition and stability are particularly important for the production of alloys designed for the casting of dental restorations and appliances. Such elements must have an exceptionally-smooth surface, free of roughness which is detectable to the tongue and which increases the surface area for attack by the atmosphere, foods, body acids and by fluoride-containing dental treatment preparations.

The improved dental casting alloys of the present invention are produced by using known alloying methods to incorporate the required minor amounts of the corrosion-inhibitor, preferably a mixture of similar amounts of ruthenium and rhenium, and, if desired for improved oxidation-resistance, the required amount of rare earth metal, preferably cerium. The most preferred compositions contain ruthenium and cerium.

Generally, the pure titanium or base titanium alloy is melted in the presence of the additive metal(s) and uniformly alloyed therewith to form a homogeneous improved alloy within which the additive metal is dissolved. The solid solution alloy preferably is reduced to fine powder form for final use, such as addition to the melt crucible of a dental casting machine for melting and flow into a dental casting mold.

The present alloys are suitable for the production of dental castings according to known procedures, such as the centrifugal casting method disclosed in U.S. Pat. No. 4,700,769, for example. Such method permits the formation of custom molds corresponding exactly to the appliance, inlay, crown, bridge or denture required by each particular patient. The present titanium alloys have the necessary melting and flow properties to fill such custom molds on a centrifugal casting apparatus and to produce castings having the desired corrosion-resistance, oxidation resistance and smooth surface properties.

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

I claim:

1. A titanium dental restoration having improved resistance to corrosion and/or oxidation under conditions of use in the mouth, comprising a molded alloy of a biocompatible base titanium alloy, having alloyed therewith from about 0.01% to 5.0% by weight of at least one metal selected from the group consisting of noble metals, rhenium, yttrium, hafnium and cerium.

2. A titanium dental restoration according to claim 1 in which said base titanium alloy comprises titanium, aluminum and a third metal selected from the group consisting of tin, niobium and vanadium.

3. A titanium dental restoration according to claim 1 in which said base titanium alloy is selected from the group consisting of Ti-5Al-2Sn, Ti-6Al-7Nb and Ti-6Al-4V.

4. A titanium dental restoration according to claim 1 in which said noble metal comprises 0.001 to 1.0% by weight of ruthenium.

5. A titanium dental restoration according to claim 1 comprising a mixture of ruthenium and rhenium.

6. A titanium dental restoration according to claim 1 in which said metal comprises 0.01 to 1.0% by weight of cerium.

7. A titanium dental restoration according to claim 1 comprising ruthenium and cerium.

8. A titanium dental restoration according to claim 1 which includes at least one metal from the group consisting of noble metals and rhenium and also at least one metal from the group consisting of yttrium, hafnium and cerium.

9. A titanium dental restoration according to claim 1 comprising from 0.1% to 1.0% by weight of a noble metal and/or rhenium.

10. A titanium dental restoration according to claim 1 comprising from 0.01% to 1.0% by weight of yttrium, hafnium and/or cerium.

11. A titanium dental restoration having improved resistance to corrosion and oxidation under conditions of use in the human mouth, comprising a molded biocompatible base alloy of titanium, aluminum and another metal selected from the group consisting of tin, niobium and vanadium, having alloyed therewith from about 0.01% to 5.0% by weight of a corrosion-inhibitor comprising at least one metal selected from the group consisting of noble metals and rhenium and from about 0.01% to 5.0% by weight of at least one metal selected from the group consisting of yttrium, hafnium and cerium.

* * * * *